（12）United States Patent
O'Connor et al.

(10) Patent No.: US 7,445,936 B2
(45) Date of Patent: Nov. 4, 2008

(54) PROCESS FOR SMALL-SCALE TESTING OF FCC CATALYSTS

(75) Inventors: Paul O'Connor, Hoevelaken (NL); Edwin Mark Berends, Almere-Stad (NL); Martinus Johannes Maria Baas, Hoorn (NL); Eelko Brevoord, Hoevelaken (NL)

(73) Assignee: Albemarle Netherlands B.V., Amersfoort (NL)

( * ) Notice: Subject to any disclaimer, the term of this patent is extended or adjusted under 35 U.S.C. 154(b) by 810 days.

(21) Appl. No.: 11/057,507

(22) Filed: Feb. 14, 2005

(65) Prior Publication Data

US 2005/0145542 A1 Jul. 7, 2005

Related U.S. Application Data

(63) Continuation-in-part of application No. 10/154,190, filed on May 22, 2002, now abandoned.

(30) Foreign Application Priority Data

Jun. 5, 2001 (EP) .................................. 01202148

(51) Int. Cl.
*G01N 31/10* (2006.01)
*B01J 8/18* (2006.01)

(52) U.S. Cl. .......................... 436/37; 422/130; 422/139; 436/155; 436/159

(58) Field of Classification Search ................. 422/129, 422/130, 139–140, 145–146; 436/37, 155, 436/159–160
See application file for complete search history.

(56) References Cited

U.S. PATENT DOCUMENTS 4,325,809 A 4/1982 Bartholic ..................... 208/91

(Continued)

FOREIGN PATENT DOCUMENTS

DE 41 03 450 8/1992

OTHER PUBLICATIONS

Johnson, P. H. et al, Journal of Industrial and Engineering Chemistry 1953, 45, 849-855.*

(Continued)

*Primary Examiner*—Arlen Soderquist
(74) *Attorney, Agent, or Firm*—Jeremy J. Kliebert

(57) ABSTRACT

The present invention pertains to A cyclic process for testing FCC catalysts with resid feedstock on a small scale wherein in a first cycle:
 a) the feed to be cracked is heated to a temperature between 50 and 500° C.,
 b) the heated feed is injected into a riser reactor containing the FCC catalyst to be tested having a temperature between 500 and 800° C., the injection time being less than 2 seconds,
 c) an inert gas is injected into the lower end of said reactor riser together in the vicinity of the feed injection in a volume ratio of inert gas to vaporized feed of about 0.03 and 10, the mixing of feed and inert gas occurring in said riser reactor;
 d) the feed is contacted with the FCC catalyst under fluidized conditions for a contact time of less than 8 seconds;
 e) the feed is stripped from the FCC catalyst and the properties of the product are analyzed; and
 in a second cycle a quench liquid is injected into said riser reactor in an amount of up to about 20 wt. % of said feed so as to reduce the temperature in said riser reactor and minimize undesirable secondary reactions.

The invention also comprises the apparatus employed to carry out the process. With the process of the invention the mass transfer and diffusion limitations of commercial FCC units are properly simulated.

10 Claims, 1 Drawing Sheet

U.S. PATENT DOCUMENTS

| | | | | |
|---|---|---|---|---|
| 4,419,328 A | * | 12/1983 | Walsh | 422/62 |
| 4,459,203 A | | 7/1984 | Beech et al. | 208/113 |
| 5,102,628 A | * | 4/1992 | De Lasa | 422/140 |
| 5,318,691 A | | 6/1994 | Muldowney | 208/113 |
| 6,069,012 A | | 5/2000 | Kayser | 436/37 |

OTHER PUBLICATIONS

Corella, J. et al, Industrial & Engineering Chemistry Product Research and Development 1986, 25, 554-562.*

Kraemer, D. W. et al, Industrial & Engineering Chemistry Research 1988, 27, 2002-2008.*

Brevoord, E. et al, Preprints—American Chemical Society, Division of Petroleum Chemistry 1995, 40, 501-504.*

Pekediz, A, et al, Industrial & Engineering Chemistry Research 1997, 36, 4516-4522.*

Alvarez, A. et al, Preprints—American Chemical Society, Division of Petroleum Chemistry 1998, 43, 172-176.*

Jakkula, J. et al, Proceedings of the World Petroleum Congress 1998, 15th(vol. 2), 736-737.* de la Puente, G. et al, Industrial & Engineering Chemistry Research 1999, 38, 368-372.*

Schuurman, Y. et al, Chemical Engineering Science 1999, 54, 3619-3625.*

Yung, K. Y. et al, Preprints—American Chemical Society, Division of Petroleum Chemistry 2000, 45, 284-285.*

Rawlence et al.; *FCC Catalyst Performance Evaluation; Applied Catalysis*, vol. 43 (1988) pp. 213-237.

Lappas et al.; Separation, Characterization and Catalytic Cracking Kinetics of Aromatic Fractions Obtained from FCC Feedstocks; *Applied Catalysis, A: General 152* (1996) pp. 7-26.

Helmsing et al.; Short Contact Time Experiments in a Novel Benchscale FCC Riser Reaction; *Chemical Engineering Science*, vol. 51, No. 11, (1996) pp. 3039-3044.

Ceriqueria et al.; Mathematical Modeling and Simulation of Catalytic Cracking of Gasoil in a Fixed Bed: Coke Formation; *Applied Catalysis A: General 164* (1997) pp. 35-45.

Cerqueira et al.; Mathematical Modeling of Deactivation by Coke Formation in the Cracking of Gasoil; *Stud. Surf. Sci. Catal. 111;* Catalyst Deactivation (1997) pp. 303-310.

Wallenstein et al.; *Microactivity Testing of FCC Catalysts at Short Contact-Times and High Temperatures and Comparison With Riser Pilot Plant Evaluations; AlChE, Spring National Meeting,* New Orleans, Mar. 8-12, 1998.

P. O'Connor et al.; *A Microscale Simulation Test for FCC Development; J. Am. Chem. Soc., Div. Pet. Chem.* 33 (4); (1988) pp. 656-662.

Margolis et al.; *The Impact of Microactivity Test Conditions on Product Yields and Properties; AlChe Symposium Series,* (1992) No. 291, vol. 88, pp. 82-87.

O'Connor et al.; *A Microscale Simulation Test for Fluid Catalytic Cracking; ACS Symposium,* Series No. 411 (1989), pp. 135-147.

Biwas et al.; Recent Process- and Catalyst-Related Developments in Fluid Catalytic Cracking; Applied Catalysis, 63 (1990) pp. 197-258.

Carter et al.; FCC Catalyst Selection; *Hydrocarbon Processing*, (1989) pp. 63-64.

Talman et al.; Development of a Downer Reactor for Fluid Catalytic Cracking; *Chemical Engineering Science 54* (1999) pp. 2123-2130.

Moorehead et al.; Microactivity Evaluation of a FCC Catalyst in the Laboratory: Principals, Approaches and Applications; *Studies in Surface Science and Catalysis;* vol. 76 (1993) pp. 223-255.

O'Connor et al.; Accessible FCC Catalysts for Short Contact Time Cracking; Prepr. Am. Chem. Soc. Div. Pet. Chem. (1996) pp. 359-360.

* cited by examiner

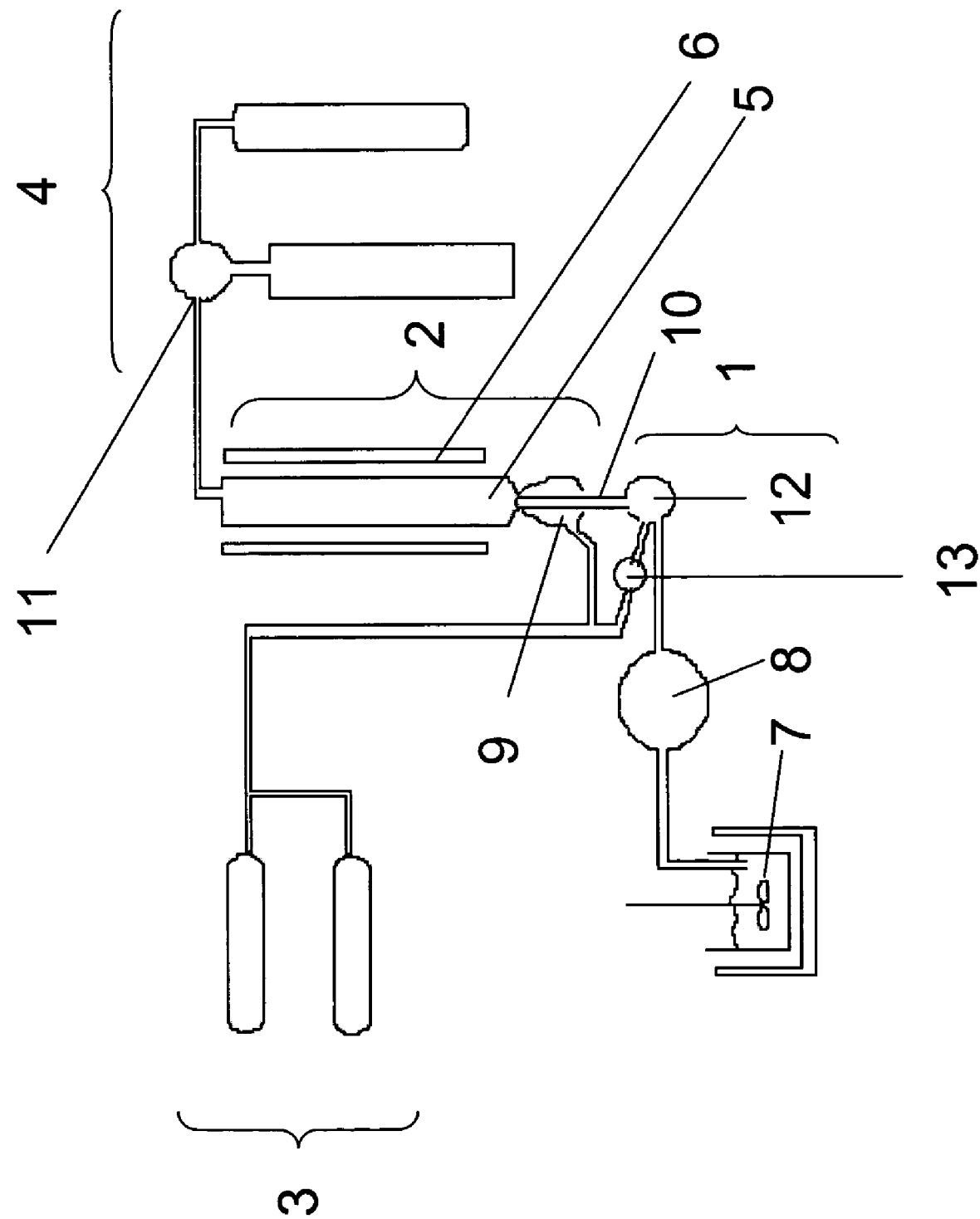

PROCESS FOR SMALL-SCALE TESTING OF FCC CATALYSTS

CROSS REFERENCE TO RELATED APPLICATION

This application is a Continuation-in-Part of application Ser. No. 10/154,190, filed May 22, 2002 now abandoned and claims priority from European Patent Application Serial Number 01202148.1, filed Jun. 5, 2001, both applications incorporated herein by reference in their entirety.

BACKGROUND OF THE INVENTION

1. Field of the Invention

The present invention relates to a process and an apparatus for testing FCC catalysts on a small scale for evaluation of the fluid catalytic cracking processes with particular regard to catalysts, feedstocks, and process parameters.

2. Prior Art

Fluid catalytic cracking is the dominant catalytic process for producing transportation fuels and chemical feedstocks world-wide. Consequently, extensive effort has gone into developing useful small-scale tests pertinent to this process for the purposes of developing improved catalysts, quantifying and correlating the cracking character of various feedstocks based on their respective properties, understanding the implications of different process conditions, and improving commercial process design.

Two broad approaches commonly used in small-scale studies of the fluid catalytic cracking process are continuous processing units and batch processing units. The continuous processing units are basically scaled-down versions (bench or pilot-scale riser reactors) of commercial operating units and are typically very complex systems that are expensive to construct, operate, and maintain. Such a small-scale continuous process test device is described in Chem. Eng. Sci. (1996), 51(11), 3039-3044. In addition, compared to small-scale batch cracking units, such small-scale continuous cracking units require large samples of catalyst and feed. Batch processing units use a single charge of catalyst (typically less than 200 g) and process a small sample mass of feed that is usually injected into the catalyst for a period of time of the order of a minute. The ratio of catalyst mass to feed mass is referred to as the catalyst-to-oil ratio and typically ranges from 3 to 10. Batch processes provide considerable cost and speed advantages over continuous units for laboratory studies, primarily because of their relative simplicity and their smaller scale.

The most commonly used batch process is the so-called microactivity test (MAT). This test is described in ASTM D-3907-86. Said test is the main tool for basic FCC research and catalyst and feedstock evaluation and monitoring. See for instance, Applied Cat., A: General 152 (1997), 7-26, Applied. Cat., A (1997), 164 (1-2), 35-45, Stud. Surf. Sci. Catal. (1997) 111 (catalyst deactivation 1997), 303-310, Catalyst. Cracking, AIChE, Symposium Series (1992) No. 291, Vol. 88, 82-87, and AIChE (1998) Spring National Meeting, New Orleans 3/8-12/8. Despite its widespread use, the possibilities to extrapolate the results obtained from a MAT test to full-scale FCC operations are limited owing to the wide difference between conditions in the MAT test and those in full-scale FCC operation. Below, the conditions in full-scale FCC operation and the conditions in the MAT test are listed.

| | ASTM-MAT | Full-scale FCC |
|---|---|---|
| reactor type | fixed bed | fluidized bed, riser |
| feed dispersion | no | more than 2% steam |
| preheat | no | fast |
| injection time (s) | 14 | 0–1 |
| catalyst/feed contact time (s). | 75 | 2–10 |
| catalyst temperature (° C.) | 483 | 650–750 |
| pressure (PSIG) | atmospheric | 10–20 |

As a result of these wide differences in conditions, the MAT test does not give a realistic prediction of the selectivities of catalysts in real FCC units. This has been studied in Applied Cat. 63 (1990) 197-258 and Applied Cat. 43 (1988) 213-237. For this reason other tests have been developed, such as the microsimulation test (MST) from Akzo Nobel as described in J. Am. Chem. Soc., Div. Pet. Chem. (1988) 33(4), 656-62 and in ACS. Symp. Series, No. 411, 135-147 (1989). In this test a catalyst/feed contact time of 15 seconds is realized, which is more in line with real FCC processing than the catalyst/feed contact time of 75 seconds in the ASTM-MAT test. In Hydrocarbon Processing, Sept. 1989, 63-4, a microactivity test is described with a contact time of 18 seconds and a cracking temperature of 510° C.

In Chem. Eng. Sci. 64 (1999) a bench-scale FCC test device is described with very short contact times (50-500 ms), but this device is a downflow device using catalyst temperatures of about 400-600° C. and thus not a proper simulation device for real FCC units, which contain upflow riser reactors.

In U.S. Pat. No. 6,069,012 a laboratory-scale fluid catalytic cracking apparatus is described. Said apparatus includes a reactor having a removable feed injector to vary the catalyst/feed contact time. The feed injector is inserted downwards into the catalyst bed. Relatively large amounts of catalyst (9 g in the examples) are used in this apparatus. The injection time of this apparatus is not mentioned. Although it is indicated that the catalyst bed is fluidized, it is a so-called slow, fixed fluidized bed which does not resemble the fast fluidized beds in a full-scale FCC unit.

In the design illustrated in Johnson, P. H. et al, *Journal of Industrial and Engineering Chemistry*, 1953, 45, pages 849-562 there is shown an apparatus for a laboratory test method by which stripping and oil go via the same line, via the oil preheater, towards the reactor. The oil is not directly injected into the reactor but is stripped by nitrogen towards the oil preheater and then at least partly evaporates before it enters the reactor.

In the paper O'Connor et al., *Accessible FCC Catalysts for Short Contact Time Cracking*; Prepa. Am. Chem., Soc. Div. Pet. Chem (1966) Pgs. 359-360, a Micro Simulation Test is described, with short injection and contact times, but a very large amount of inert gas (volume ratio of inert gas to hydrocarbon greater than 50) was employed to obtain good feed-catalyst mixing and to control the reactor riser temperature.

Although the microsimulation tests give a more accurate prediction of catalyst selectivity in general, with the necessity to process heavier feedstocks, to obtain higher gasoline motor octanes, and to fulfil the environmental specifications on $NO_x$, $SO_x$ as well as sulfur levels in gasoline, there is an ongoing need for reproducible tests which also accurately simulate resid FCC operations, operations at higher riser temperatures, operations with higher catalyst to oil ratios, etc.

SUMMARY OF THE INVENTION

Accordingly, in one embodiment the present invention is a cyclic process for testing FCC catalysts with resid feedstock on a small scale wherein in a first cycle:
a) the feed to be cracked is heated to a temperature between 50 and 500° C.,
b) the heated feed is injected into a riser reactor containing the FCC catalyst to be tested having a temperature between 500 and 800° C., the injection time being less than 2 seconds,
c) an inert gas is injected into the lower end of the reactor riser together in the vicinity of the feed injection in a volume ratio of inert gas to vaporized feed of about 0.03 and 10, the mixing of feed and inert gas occurring in the riser reactor;
d) the feed is contacted with the FCC catalyst under fluidized conditions for a contact time of less than 8 seconds;
e) the feed is stripped from the FCC catalyst and the properties of the product are analysed; and
in a second cycle a quench liquid is injected into the riser reactor in an amount of up to about 20 wt. % of said feed so as to reduce the temperature in said riser reactor and minimize undesirable secondary reactions.

Other embodiments of the invention encompass details relating to process conditions and riser reactor injection streams, all of which are hereinafter described.

BRIEF DESCRIPTION OF FIG. 1

FIG. 1 is a schematic representation of the apparatus of the invention.

DETAILED DESCRIPTION OF THE INVENTION

With the process according to the invention the mass transfer and diffusion limitations of commercial FCC units are properly simulated. In Prepr. Am. Chem. Soc., Div. Pet. Chem. (1996), (41(2), 359-60, a lab-scale short contact time test is described wherein a short contact time and a short injection time are mentioned. However, it is not indicated how this short injection time is obtained. Further the feed temperature and the catalyst temperature are not mentioned. As indicated above, these features are essential to proper FCC simulation.

In this context, the term small-scale usually refers to the use of less than 200 g of catalyst. However, in the process according to the invention typically less than 10 g of catalyst, preferably less than 3 g of catalyst, more preferably less than 2 g of catalyst, and most preferably less than 1 g catalyst can be used without hampering the reproducibility and accuracy of the test.

The feed to be cracked is heated to a temperature between 50 and 500° C., preferably between 50 and 100° C. Optionally, the feed is heated under a pressure above atmospheric pressure.

An injection time of less than 2 seconds is essential to proper simulation of the mass transfer and diffusion limitations in full-scale FCC units. Especially when cracking heavier feeds such as resids, a short injection time becomes very important.

The short injection time can be realized with the use of a high-pressure pump. Suitable high-pressure pumps are the ones known from cars with injection engines, for instance high-pressure diesel injection pumps from Bosch®, Volkswagen®, and General Motors®. High-pressure diesel injection pumps have an injection time of less than 2 seconds. The injector takes care of the injection and atomisation of the feed into the catalyst bed. The newly developed injection pumps even have injection times of less than 1 second. Volkswagen® has developed high-pressure injection pumps with injection times of the order of milliseconds. With these types of injection pumps (having injection times of the order of milliseconds) even newly developed FCC operations can be simulated wherein the feed is pre-vaporised. These newly developed FCC operations are described in patent applications in the name of Shell and Petrobras. Therefore, an injection time of less than 1 second, or more preferably of less than 0.5 seconds is preferred, because in full-scale FCC units the injection time is also less than 1 second, of the order of 0.5 seconds. In pre-vaporised FCC operation the injection time is even shorter.

In the method according to the invention the FCC catalyst is contacted with the feed under fluidized conditions. This is realized by injecting the atomized oil feed and the carrier gas into the lower part of the riser reactor. In this way a fast fluidized bed is obtained which resembles the fluidized beds in full-scale FCC units. In fixed beds a coke gradient is formed over the hardware and the catalyst bed, which lowers the mass balance and allows only the light part of the feed to contact the catalyst. The use of a fluidized bed ensures a proper contact of the entire feed with the catalyst. As mentioned above, it is essential that the catalyst/feed contact time is less than 8 seconds, preferably less than 5 seconds, most preferably less than 3 seconds.

It is essential that the feed and inert gas be independently injected into the reactor riser and not pre-mixed prior to introduction into the reactor riser. Pre-mixing would result in a relatively large volume of fluid that would have to be passed into the reactor riser that would render an injection time as short as that required by the present invention to be impossible.

The invention requires that the an inert gas be injected into the riser reactor in the vicinity of the feed injection, which means close enough to the point of feed injection to achieve thorough mixing of gas and feed and dispersion of the feed and catalyst.

In the above mentioned Johnson et al article, between the point of injection and the reactor, axial and radial dispersion of the oil takes place and some of the injected oil would not leave the lining at all, but would just stick to the walls. The result would be oil being introduced to the reactor at delayed response and without pulse injection. Thus, in Johnson et al the oil could only be introduced to the reactor during a much longer period than just the time for a single pulse from the injector.

Another essential requirement of the invention is that it comprises a cyclic process. That means following injection of feed and inert gas, which is the feed cycle, there is a second cycle, the quench cycle, wherein a quench liquid is injected into the riser reactor in an amount of up to about 30 wt. % of the feed. This will serve to reduce the temperature in the riser reactor and make possible the very low inert gas to feed ratio in the feed cycle, since the inert gas need not be relied upon to control the riser reactor temperature.

The quench liquid could be any liquid compatible with the reaction mixture in the riser reactor, preferably selected from the group consisting of water, gasoline and light cycle oil.

The ability to so accurately simulate a commercial full sized FCC unit in a small scale sized unit by employing the cyclic process of the present invention was surprising and unexpected. The accomplishment lies in achieving heat balance and temperature control in the reactor riser with a very small inert gas to feed ratio that has not been previously accomplished, notwithstanding the long felt need to do so in a small scale unit. The use of a cyclic process with a quench cycle required thinking "outside the box", since this concept is unknown in the conventional or full scale FCC process.

The pressure in the reactor can be up to 40 psig, preferably 5-30 psig, more preferably 5-10 psig.

The process according to the invention is suitable for testing FCC catalysts with any conventional FCC feed, such as Vacuum Gas Oil, gas oil (aromatic, paraffinic, naphthenic), light cycle oil, and heavy vacuum distillate. However, one of the major advantages of the method according to the invention over prior art test methods is that it enables catalyst testing for the fluidized cracking of resid feeds in realistic conversion and yield with proper reproducibility. For instance, the process is highly suitable for feedstocks having a Conradson Carbon Residue of up to 15 wt %, more particularly a Conradson Carbon residue of between 9 and 15 wt %.

Prior to the process according to the invention, the catalyst to be tested may be submitted to a deactivation procedure, such as steam deactivation, cyclic deactivation with Ni and/or V, V deactivation followed by mild steam deactivation, etc. An overview of several deactivation procedures is given in Studies in Surface Sci. and Cat. Vol 76 (1993) 223-255. Deactivation procedures are known in the field and need no further elucidation here.

The present invention also pertains to an apparatus for conducting the process according to the invention. Said apparatus, with reference to the schematic representation given in FIG. 1, comprises an oil feed section (1) and a gas feed section (3), which are connected to the lower part of a riser reactor section (2), which is connected to a product collection section (4). The riser reactor section comprises a reactor (5) and heating means (6), while the oil feed section comprises an oil storage vessel (7) and a high-pressure injection pump (8). Optionally, the oil storage vessel (7) is heated and stirred.

As mentioned above, a high-pressure injection pump is necessary to ensure a feed injection time of less than 2 seconds. The feed is injected and atomized through a nozzle into the lower end of the riser reactor. The injection time is controlled by moving the control rod of the injection pump. The amount of oil injected is controlled by the frequency and the stroke of the injection pump.

The gases needed for fluidizing and stripping the catalyst bed are injected into the lower end of the riser reactor. Usually nitrogen is used for this purpose, but any inert gas is suitable. The fluidization gas is guided to the lower end of the riser reactor both directly and together with the oil feed. Oxygen or air may be used to burn the coke from the catalyst. In order to control the gas flow, mass flow controllers can be used.

The riser reactor section comprises a reactor and heating means. The heating means can be any heating means commonly used in laboratories, such as an oven, heating coils, oil baths, etc. Preferred is an oven. The reactor preferably has a conical lower end. The lower end of the reactor has a fluidization gas inlet (9) and what during the feed injection cycle is oil feed inlet (10). The oil passes through valve (12) on the way to inlet (10).

The product collection section is divided up into a liquid and a gas collection system. Gases that leave the system are partly condensed in a receiver (11), which is mounted in a bath that, depending on the applied feedstock, has a temperature between −5 and −30° C., preferably between −10 and −15° C. The non-condensable gases are collected in a gas bottle. The yields of liquid product and gas products are determined by conventional analytical methods known in the art.

The quench liquid is maintained in a sample loop that is connected to multi-port valve (13). The quench cycle is initiated by switching the multi-port valve (13). The stripping gas is redirected via the sample loop, which allows the quench liquid to be injected into the catalyst bed via valve (12) and line (10).

During quenching both quench and stripping gas enter the reactor. The amount of quench is up to 30 wt % based on feed. This amount may be adjusted by choosing a different sample loop and stripping gas is used as transportation for the quenching agent. During a performance run the quench cycle is started by switching valve (13) only once at a defined time interval directly after oil injection.

EXAMPLES

Example 1

Table 1 compares the conversion and cracking products formed during a cracking process in a full-scale FCC unit (FCCU) and in a testing apparatus according to the invention (SCT-RT).

The feed temperature in the testing process according to the invention was 85° C., the feed injection temperature 720° C., the pressure in the reactor was 5 psig, the injection time 1.0 s, and the average catalyst-feed contact time between 2 and 4 seconds. 18 grams of catalyst were used in this small-scale test.

The cat-to-oil ratio in the full-scale FCC unit and the small-scale testing apparatus was 5.9 and 6.0, respectively.

Table 1 shows that with an increase in pressure of about 10 psig, the increase in conversion and the change in product yield in the testing apparatus and in the FCC unit are comparable.

TABLE 1

|  | SCT-RT | FCCU |
| --- | --- | --- |
| Delta p (psig) | +9 | +10 |
| Delta Conversion (wt %) | +2.2 | +2.4 |
| Yield shifts (wt %): |  |  |
| Propene/propane | −0.03 | −0.03 |
| Butenes/butane | −0.06 | −0.06 |
| Gasoline | +0.6 | +0.6 |
| LCO | −0.2 | −0.9 |
| Bottoms | −2.0 | −1.4 |
| Coke | +0.5 | +0.9 |

Example 2

Table 2 compares the conversion in a full-scale FCC unit and in a testing apparatus according to the invention for two different catalysts. Catalyst A is a conventional FCC catalyst; Catalyst B is a conventional FCC catalyst that has been severely deactivated in the FCC unit, resulting in a reduced accessibility. The accessibility was measured using the test disclosed in non pre-published European Patent Application No. 01202147.3.

The feed temperature in the testing process according to the invention was 85° C., the feed injection temperature 640° C., the pressure in the reactor was atmospheric, the injection time 1.0 s, and the average catalyst-feed contact time between 2 and 4 seconds. 18 grams of catalyst were used in this small-scale test.

Table 2 indicates 15 and 9 wt % lower conversions for catalyst B and catalyst A, respectively.

TABLE 2

|  | Catalyst A | Catalyst B |
| --- | --- | --- |
| FCCU conversion (wt %) | Base | −15 |
| SCT-RT conversion (wt %) | Base | −9 |
| Akzo Accessibilty Index | 5.9 | 2.6 |
| SA-BET (m$^2$/g) | 113 | 112 |
| PV-micro (ml/g) | 0.038 | 0.038 |
| SA-Meso (m$^2$/g) | 31 | 30 |
| Al$_2$O$_3$ (wt %) | 34.1 | 33.7 |
| RE$_2$O$_3$ (wt %) | 1.99 | 1.88 |
| Na$_2$O (wt %) | 0.64 | 0.55 |
| Ni (ppm) | 2,915 | 2,787 |
| V (ppm) | 4,029 | 2,960 |

Example 3

The performance of two different FCC catalysts is compared in a full-scale FCC unit (FCCU) and in a testing apparatus according to the invention (SCT-RT). The difference between these two catalysts in catalyst-to-oil ratio, coke formation, and bottoms formation is presented in Table 3.

The feed temperature in the testing process according to the invention was 85° C., the feed injection temperature 640° C., the pressure in the reactor was 5 psig, the injection time 1.0 s, and the average catalyst-feed contact time between 2 and 4 seconds. 18 grams of catalyst were used in this small-scale test.

It is clear that the same trends, showing small differences in performance, can be observed in the testing apparatus according to the invention and in the full-scale FCC unit. As the skilled man knows, such trends cannot be observed with the conventional microactivity test (MAT).

TABLE 3

|  | SCT-RT | FCCU |
| --- | --- | --- |
| Cat-to-oil ratio | +1.0 | +1.8 |
| Delta coke (%) | −0.11 | −0.18 |
| Bottoms (wt %) | −3.7 | −1.8 |

Example 4

Table 4 shows the conversion and recovery of 15 grams of a conventional FCC catalyst at a constant cat-to-oil ratio during the cracking of feeds with different Conradson carbon residues (CCR) in the testing apparatus according to the invention. It is clear from this Table that the process according to the invention is highly suitable for studying the cracking of heavy feedstocks.

TABLE 4

|  | Feed A | Feed B | Feed C |
| --- | --- | --- | --- |
| Feed temperature (° C.) | 85 | 85 | 140 |
| Feed injection temperature (° C.) | 680 | 680 | 680 |
| Feed injection time (s) | 1.0 | 1.0 | 1.0 |
| CCR (wt %) | 3.4 | 5.9 | 9.7 |
| Spec. Gravity, 15° C. (g/ml) | 0.92 | 0.93 | 0.98 |
| Cat-to-oil ratio | 5.0 | 5.0 | 5.0 |
| Conversion (wt %) | 67.6 | 73.7 | 69.0 |
| Recovery (wt %) | 100.4 | 99.8 | 102.0 |

Example 5

Table 5 shows an example of a gasoline quench on the cycle oil properties of an SCT-RT cracking product, demonstrating an improvement in cycle oil properties for the quench experiment.

The amount of quench was 15.5 wt % on feed, injected into the catalyst bed at 1 second after oil injection.

TABLE 5

| Quench in SCT-RT | | |
| --- | --- | --- |
|  | No quench | Quench |
| Conversion (wt %) | 77.8 | 74.8 |
| LCO composition |  |  |
| Paraffins | 19.7 | 21.5 |
| n-Paraffins | 5.5 | 6.2 |
| Iso-paraffins | 13.8 | 14.9 |
| Naphtenes | 0.29 | 0.44 |
| Olefins | 1.8 | 4.0 |
| Aromatics | 78.5 | 74.4 |
| Mono-Aromatics | 4.4 | 5.0 |
| Napthenic Mono Aromatics | 11.3 | 12.6 |
| Di-Aromatics | 46.7 | 42.5 |
| Napthenic Di-Aromatics | 11.5 | 10.6 |
| Tri-Aromatics | 11.5 | 10.6 |
| Napthenic Tri-Aromatics | 0.0 | 0.0 |
| HCO composition |  |  |
| Paraffins | 14.6 | 37.4 |
| n-Paraffins | 10.9 | 25.4 |
| Iso-paraffins | 2.8 | 8.6 |
| Naphtenes | 0.89 | 3.34 |
| Olefins | 0.0 | 0.0 |
| Aromatics | 85.4 | 62.6 |
| Mono-Aromatics | 0.1 | 0.2 |
| Napthenic Mono-Aromatics | 1.2 | 1.3 |
| Di-Aromatics | 0.0 | 0.0 |
| Napthenic Di-Aromatics | 4.4 | 3.2 |
| Tri-Aromatics | 39.9 | 30.8 |
| Napthenic Tri-Aromatics | 4.1 | 3.0 |
| Pyrenes | 22.2 | 15.5 |
| tetra(+)-aromatic | 13.5 | 8.5 |

It can be seen from the results given in Table 5 that, among other things, quenching accomplishes the following:

1. It lowers catalyst bed temperature at some point in the reaction (in this case at 1 second after oil injection) to avoid secondary cracking reactions, like the formation of aromatics.
2. It creates extra stripping flow in the reactor creating a shorter vapor contact time and more efficient (faster) stripping of the catalyst.
3. It may have an impact on the cracking reaction in this case, because gasoline is used as quench agent.
4. It improves cycle oil quality by showing a lower aromatic content and higher paraffin content.

The invention claimed is:
1. A cyclic process for testing FCC catalysts with resid feedstock on a small scale wherein in a first cycle:
   a) the feed to be cracked is heated to a temperature between 50 and 500° C.,
   b) the heated feed is injected into a riser reactor containing the FCC catalyst to be tested having a temperature between 500 and 800° C., the injection time being less than 2 seconds,
   c) an inert gas is injected into the lower end of said reactor riser together in the vicinity of the feed injection in a volume ratio of inert gas to vaporized feed of about 0.03 and 10, the mixing of feed and inert gas occurring in said riser reactor;

d) the feed is contacted with the FCC catalyst under fluidized conditions for a contact time of less than 8 seconds;

e) the feed is stripped from the FCC catalyst and the properties of the product are analyzed; and in a second cycle a quench liquid is injected into said riser reactor in an amount of up to about 20 wt. % of said feed so as to reduce the temperature in said riser reactor and minimize undesirable secondary reactions.

2. The process of claim 1 wherein the injection time is less than 1 second.

3. The process of claim 2 wherein the injection time is less than 0.5 seconds.

4. The process of claim 1 wherein the contact time is less than 5 seconds.

5. The process of claim 4 wherein the contact time is less than 3 seconds.

6. The process of claim 4 wherein the contact time is less than 0.1 seconds.

7. The process of claim 1 wherein the pressure in the reactor is 5-30 psig.

8. The process of claim 1 wherein the feed is a resid feedstock having a Conradson Carbon Residue of up to 15 wt %.

9. The process of claim 8 wherein the feed is a resid feedstock having a Conradson Carbon Residue between about 9 and 15 wt %.

10. The process of claim 1 wherein said quench liquid is selected from the group consisting of water, gasoline and light cycle oil.

* * * * *